United States Patent [19]
Bulstra et al.

[11] Patent Number: 6,102,914
[45] Date of Patent: Aug. 15, 2000

[54] DETACHABLY CONNECTING CAP FOR A SCREW USED IN ORTHOPAEDIC SURGERY

[75] Inventors: Sjoerd Bulstra, Maastricht; Teake Bulstra, Voorburg; Leo H. Koole, Gulpen, all of Netherlands

[73] Assignee: Biomat B.V.

[21] Appl. No.: 09/230,274

[22] PCT Filed: Jul. 23, 1997

[86] PCT No.: PCT/NL97/00439

§ 371 Date: Sep. 30, 1999

§ 102(e) Date: Sep. 30, 1999

[87] PCT Pub. No.: WO98/03209

PCT Pub. Date: Jan. 29, 1998

[30] Foreign Application Priority Data

Jul. 23, 1996 [EP] European Pat. Off. .............. 96202084

[51] Int. Cl.$^7$ ................................................ A61B 17/84
[52] U.S. Cl. .............................. 606/72; 606/73; 606/76; 600/426

[58] Field of Search .................................. 606/60, 65, 72, 606/73, 76, 130; 600/426

[56] References Cited

U.S. PATENT DOCUMENTS

| | | | |
|---|---|---|---|
| 3,918,440 | 11/1975 | Kraus | 602/2 |
| 5,372,503 | 12/1994 | Elia | 433/215 |
| 5,730,130 | 3/1998 | Fitzpatrick et al. | 600/426 |

*Primary Examiner*—Michael Buiz
*Assistant Examiner*—David O. Reip
*Attorney, Agent, or Firm*—Welsh & Katz, Ltd.

[57] ABSTRACT

The present invention relates to a bone screw cap or stopper, comprising a shank (5) that fits closely to the outer contour of the head (2) of the screw and means (4) for detachably connecting the cap or stopper to the bone screw (1). Especially this stopper comprises an extended shank whose section is at least as large as the largest sectional part of the bone screw, and the length of the extended shank is preferably such that the end of the stopper remote from the bone screw extends to the subcutis.

5 Claims, 1 Drawing Sheet

DETACHABLY CONNECTING CAP FOR A SCREW USED IN ORTHOPAEDIC SURGERY

The present invention lies in the field of orthopaedic surgery and relates more in particular to caps for screws which are used in this field. These screws are referred to in this description and the attached claims as "bone screws".

Bone screws are widely used as temporary medical implants for the fixation of skeletal fractures and/or for the fixation of orthopaedic implants. Important areas of application are (i) fixation of the spinal cord after a geometric correction, (ii) healing of fractures in the knee, heel, elbow or hip, and (iii) fixation of hip prostheses. Bone screws are generally made of a metallic material, e.g. of titanium, cobalt-chrome alloys and stainless steel. The metallic materials used should have an excellent biocompatibility in contact with bone and surrounding tissues.

As said, bone screws generally are temporary implants. They play an important role in keeping the integrity of the bone tissue after, e.g. a fracture.

The length of the bone screw used by the orthopaedic surgeon is normally as short as possible. The shorter a bone screw is the less discomfort is caused to the body, while the bone screw can be screwed down or fixated more tightly.

In the course of the several months or years that the bone screw stays in the body, bone growth leads to reinforced bone structures. This makes the presence of the bone screw superfluous, so that the bone screw is removed in a surgical operation. In addition, removal of the bone screw eliminates possible long-term complications, such as allergic reactions and irritations.

The removal of the fixation bone screws is, contrary to what one might expect, not a straight forward operation; it is usually associated with several complications. The first problem is associated with the fact that the bone screws used normally comprise holes or grooves, such as sockets, for screwing down, and/or comprise other irregularities. These holes and so on, generally hexagonal in shape, which are normally found on top of the screw, are filled and/or surrounded with scar tissue and/or newly formed (bone) tissue. Obviously, this tissue has to be removed prior to the introduction of the screw driver in the bone screw. This removal of tissue is highly time-consuming as it has to be performed with great care. Moreover, the risk of infections increases with the operation time.

Further, the screws cannot easily be located. Although the screws are clearly visible under e.g. X-ray fluoroscopy, the images obtained only provide a two-dimensional picture, so that it is often difficult to find the exact position of the screw.

In the Russian patent application 2,026,648 it has been proposed to design an osteosynthesis screw having a head with a very specific slot. The slot has a trapezoid-section, whereby the smaller base of the trapezoid faces outward. This slot may be covered with a cap made from material which has a so-called shape memory effect, and a very specific form comprising feet to engage with the trapezoid-shaped slot, a vertical rib on its outer surface which has at least one hole in it, and a flexible insert between the screw head and the cap. In order to attach and remove the cap, heating and cooling steps are needed. It is indicated that the cap with the rib with hole(s) is advantageous for an easier location. The problem of tissue in growth in cavities or other irregularities of the screw or cap is not addressed in this document.

U.S. Pat. No. 3,918,440 discloses a device for promoting formation of bone material. The device comprises a plastic-cap locking element which fits into the socket of the head of a bone screw. The cap is attached to a coil through a connecting wire, which coil is located outside of the treated patient, for applying an A.C. signal to the bone in order to promote bone growth. The cap comprises protruding elements, such as the connecting wire, which elements in fact create similar problems in respect of the surrounding and newly formed tissue, as uncapped bone screws.

The problem underlying the present invention is to safely facilitate and accelerate the removal of bone screws in an orthopaedic operation. This problem is solved by detachably connecting a cap to the bone screw after the insertion thereof in the bone. The term "cap" is used in a broad sense and encludes stoppers, plugs and so on.

In a first aspect, the present invention relates to a bone screw cap, plug or stopper, comprising a shank that fits close to the outer contour of the head of the screw, and means for detachably connecting the cap, plug or stopper to the bone screw. The cap of the invention has a regular shape and a smooth surface, which do not allow the ingrowth of bone tissue. This cap should fit so closely to the outer contour or perimeter of the bone screw head that substantially no bone tissue can be formed between the cap and the screw. Also, the cap has a shape that permits removal of the cap from a bone screw substantially without damaging bone and/or scar tissue, when the screw is fixated to bone. This means that said shape is essentially free of protruding, idented or other elements, which would unnecessarily tear tissue when the cap is removed from a screw.

In a preferred embodiment the bone screw, cap or stopper has an extended shank, so that a bone screw extension piece is formed. This stopper comprises an extended shank whose section is at least as large as the largest sectional part of the bone screw.

This embodiment, wherein the bone screw stopper when attached to the bone screw extends from the bone, enables the surgeon to remove the screw with as less damage to tissues to the tissue as possible, whereas in current practice a deep wound has to be made. In the most preferred embodiment, the length of the extension piece is such that the end of the extension piece remote from the bone screw extends to the subcutis. In this embodiment, only a small subcutaneous incision is needed to remove the screw. Moreover, a skilled surgeon can locate the bone screw by means of the stopper, without needing X-rays; he can trace the stopper with his hands, if needed.

Although it is possible to shorten the stopper so that it ends in the subcutis, e.g. by cutting or sawing the superfluous part away, it is preferred to have available stoppers of a variety of lengths, so that the surgeon can choose therefrom after the bone screw has been applied. Cutting and sawing leads to irregular surfaces, often with sharp edges, which may lead to undesirable reactions, such as tissue ingrowth and irritations, in the body.

Since smaller incisions are sufficient, and autologous bone tissue does not have to be removed, the risk of infections is reduced considerably when using the detachable stopper of the invention.

The removal of the bone screws can hence be accomplished as follows;

after the formation of sufficient tissue to make the autologous bone tissue sufficiently strong, the location of the screw and/or the screw stopper is determined, e.g. by X-ray fluoroscopy;

the end of the screw stopper is exposed via a small incision which in the most preferred embodiment only involves an incision in subcutaneous tissues;

the screw stopper is pulled out, e.g. using a wrench, thus leaving an open channel;

a screw driver is introduced through the channel and fixed to the screw;

the screw is released and removed through the channel; and the wound is closed.

The bone screw stopper can be made of any material that does not give undesirable reactions in the body. Such materials should be biocompatible and inert to avoid any complications when the screw stoppers are in the body. Complications to be avoided are, e.g., infections, irritation, cell death, tumor formation, and so on. Suitable materials are known to the person skilled in the art, and include ceramic materials, metals, alloys, or composite materials. The manufacturing techniques are dependent on the materials used. A major concern when using different materials should be the biocompatibility. It is absolutely mandatory, especially since the intended use of the bone screw and bone screw caps in the body exceeds 30 days, that the materials show excellent biocompatibility, i.e. any unwanted effects, such as irritation, infection, tumor formation, etc. that is brought about by the implant material is untolerable.

Further, it is preferred if the material shows X-ray visibility. This feature will render the bone screw stoppers visible under routine X-ray fluoroscopy as is normally used in operations to remove the bone screws. It enables the surgeon to locate the position of the screw and the screw stopper with high accuracy. Thus, the X-ray visibility, or radio-opacity, of the material markedly contributes to the safety of the stopper. Should a radio-opaque screw stopper detach from an implanted screw, it can efficiently be retrieved through X-ray fluoroscopy.

Preferred materials for the stoppers of the present invention to be made of, are rubbery materials, in particular biocompatible, inert polymers. Such flexible materials more or less match the surrounding tissue with respect to the mechanical properties. They can be designed such that a strong press fit connection to a screw head is realized. If the screw cap is much stiffer than the surrounding tissue, it may cause some discomfort to the patient. The screw stoppers of the invention are hence most preferentially manufactured out of polymeric materials, particularly those of the methacrylate family. These polymers which may be homopolymers, copolymers, terpolymers or higher variants of polymers have excellent biocompatibility, also in contact with bone.

The most optimal materials for the manufacture of the new screw caps are methacrylate polymers that feature intrinsic X-ray visibility, since they are built-up—either completely or in part—from monomeric building blocks that contain covalently bound iodine and/or bromine. Such polymeric materials (homopolymers, copolymers, terpolymers, or higher variants) are known in the art, and described in e.g. EP-A-0 684 222 and WO-A-96/05872, which are incorporated herein by reference to describe the suitable polymer materials in detail.

It should be noted that suitable materials can be chosen from a wide variety of copolymers, homopolymers, terpolymers, and other materials can be chosen. For example, polymers of ethylmethacrylate (see example 1) or n-butylmethacrylate (see example 2) as well as of other acrylates and methycrylates can be chosen. Examples of suitable monomers are, but are not limited to: 2-hydroxyethylmethacrylate, methylmethacrylate, ethylacrylate, n-propylmethacrylate, methacrylamide, N-vinylpyrollidone, styrene, ethylene, propylene, and other molecules that contain one or more polymerizable double or triple bonds.

Furthermore, other bromine- or iodine-containing monomers can be used to render the screw caps visible with X-ray fluoroscopy. Such monomers are described in both patent applications cited above.

In another embodiment, the screw stoppers are made of a radiolucent polymer or a polymer made radiopaque through the addition of a radiopaque additive, such as barium sulfate, zirconium dioxide or other contrast fillers known in the art.

The invention will be described in further detail, while referring to the drawing. In the drawing, FIG. 1a schematically represents a bone screw FIG. 1b shows a top view of the bone screw of FIG. 1a.

FIG. 2 shows a longitudinal section of a cap of the present invention, designed to be attached to the bone screw of FIG. 1a.

FIG. 3 shows a longitudinal section of a cap or stopper having an extended shank, designed to be attached to the bone screw of FIG. 1a.

Figure 1A:
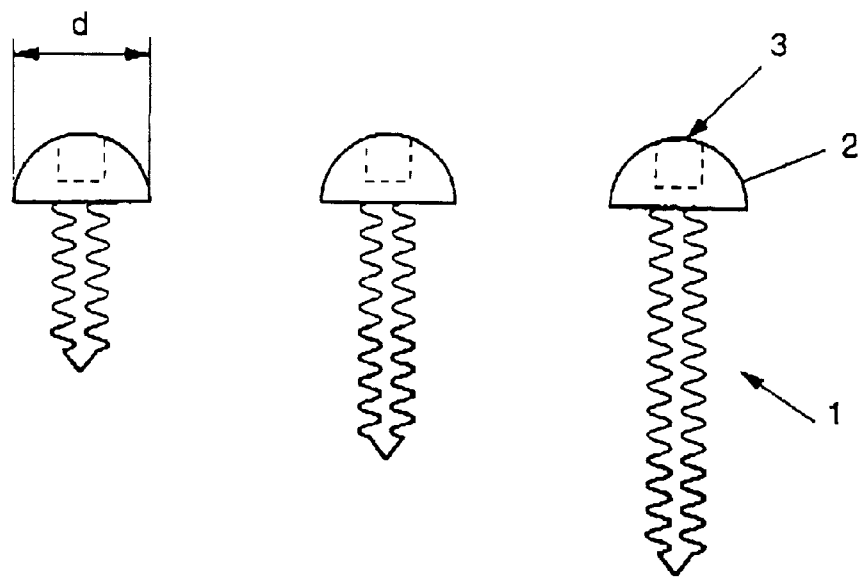
Figure 1B:
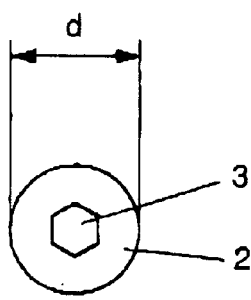

FIGS. 1a and 1b provide a side and top view of a metallic screw 1 as normally used in orthopaedic practice. The bone screw 1 contains a head 2 comprising a hole, in this embodiment a socket 3. The head 2 can however also comprise a groove or cross, or contain an extended part, such as a hexagonal extension.

Figure 2:
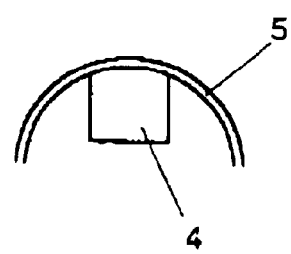

FIG. 2 shows a stopper of the present invention, which stopper contains a hexagon 4 for engagement with socket 3, and a covering means 5 that closely fits head 2. The stopper can be pushed-fixed in the socket, immediately after the bone screw has been screwed down in the bone.

Figure 3:
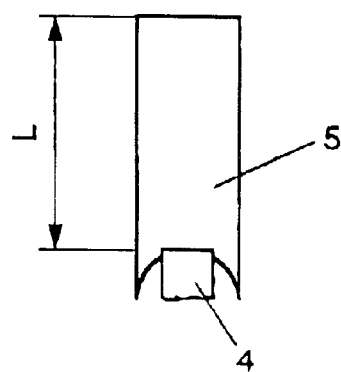

FIG. 3 shows a preferred embodiment of the stopper of FIG. 2, wherein the covering means 5 is an extended shank having length 1. The extended covering means 5 can be conical, cylindrical or shaped in another form (e.g. hexagonal), as long as the the cap closely fits to the screw.

In a preferred embodiment, the bone screw extension piece of the invention contains as means for detachably connecting the extension piece to the bone screw 1 a hexagon for engagement with a socket.

The invention will now be described in more detail, while referring to the following examples.

EXAMPLES

Example 1

Manufacture of bone screw caps out of a copolymer of ethylmethacrylate and 2-[4'-iodobenzoyl]-ethyl methacrylate formula 1).

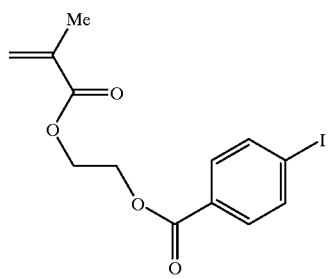

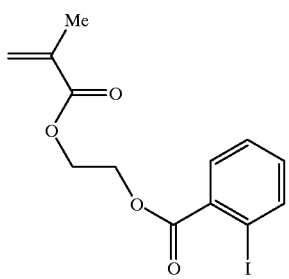

Ethylmethacrylate and the compound of formula 1 are mixed in a 4:1 (w:w) ratio, and transferred into a reaction vessel made out of Teflon. Then, pure (sublimed) α,α'-azo-bis-isobutyronitrile (AIBN) was added in a 0.5% molar concentration (i.e. mole of initiator: total moles of monomer=1:200). The reaction mixture is heated in a thermostated oil bath, interfaced with a time-temperature control system. The following time-temperature profile was then run; 0–60 min.: heat from 25 to 60° C.; 60–240 min: temperature constant at 60° C.; 240–300 min: heat to 90° C.; 300–420 min: temperature constant at 90° C.; 420–480 min: heat to 120° C.; 480–540 min: temperature constant at 120° C.; 540 min—approximately 12 h: cool to ambient temperature. The copolymer is obtained as a hard, glass-like, transparent material which closely resembles Plexi-glass in its appearance. The material is essentially free of residual monomers, as can be shown by NMR analysis. The material shows clearly X-ray fluoroscopic contras. The material is cut (sawn) into small pieces which are then used for the manufacture of the screw caps. For this, a computer-controlled drill-freese is used. Screw caps of different dimension (length of the stem, width, mushroom-like as shown in FIG. 2, formed as in FIG. 2, etc.) can be obtained in known ways via this approach. The screw caps made out of the particular copolymer described in this example are hard in comparison to surrounding (muscular) tissues.

Example 2

Manufacture of screw caps out of a copolymer of n-butylmethacrylate and 2-[4'-iodobenzoyl]-ethyl methacrylate (formula 2).

Butylmethacrylate and the compound of formula 2 are mixed in a 4:1 (w:w) ratio, and transferred into a reaction vessel made out of Teflon. Then AIBN, a temperature-labile organic peroxide, or another radical-generating species is added, preferably in a 0.5% molar concentration (i.e. mole of initiator:total moles of monomer=1:200). The reaction mixture is heated in a thermostated oil bath, interfaced with a time-temperature control system. A time-temperature profile such as the one described in Example 1 is then run. The material thus obtained is more rubbery (i.e. softer) than the material described in Example 1. This material is also essentially free of monomer. Machining into the desired screw caps is slightly more difficult, since the material is rubbery. Machining has to be performed while the material is cooled down, preferably through the use of liquid nitrogen. Screw caps of different shapes can be obtained in this way. The screw caps are softer, and show closer match with respect to the surrounding tissue.

What is claimed is:

1. A bone screw cap, comprising a shank that fits closely to an outer contour of a head of a bone screw, and means for detachably connecting the cap to the bone screw, which cap consists of an X-ray visible rubbery polymer.

2. A bone screw cap according to claim 1, comprising an extended shank whose section is at least as large as a largest sectional part of the bone screw.

3. A bone screw cap according to claim 1, wherein the shank is extended and the length of the extended shank is such that an end of the cap remote from the bone screw is adapted for extension to the subcutis.

4. A bone screw cap according to claim 1, wherein said means for detachably connecting the cap to the bone screw comprise a hexagon for engagement with a socket.

5. A bone screw cap according to claim 1, consisting of methacrylate units containing polymer having intrinsic X-ray visibility.

* * * * *